US006649775B2

(12) United States Patent
Lee et al.

(10) Patent No.: US 6,649,775 B2
(45) Date of Patent: Nov. 18, 2003

(54) PROCESS OF LACTONIZATION IN THE PREPARATION OF STATINS

(75) Inventors: Kwang-Hyeg Lee, Seongnam Si (KR); Jin-Wan Kim, Seoul (KR); Myeong-Sik Yoon, Yongin Si (KR); Kwang-Do Choi, Anyang Si (KR); Sang-Ho Lee, Anyang Si (KR); Hong-Suk Cho, Icheon Si (KR)

(73) Assignee: Cheil Jedang Corporation, Seoul (KR)

( * ) Notice: Subject to any disclaimer, the term of this patent is extended or adjusted under 35 U.S.C. 154(b) by 0 days.

(21) Appl. No.: 10/200,174

(22) Filed: Jul. 23, 2002

(65) Prior Publication Data

US 2003/0050482 A1 Mar. 13, 2003

(30) Foreign Application Priority Data

Aug. 27, 2001 (KR) .................................... 2001-0051796

(51) Int. Cl.[7] ............................................. C07D 309/10
(52) U.S. Cl. ....................................................... 549/292
(58) Field of Search .......................................... 549/292

(56) References Cited

U.S. PATENT DOCUMENTS

| 4,588,820 A | 5/1986 | Stokker |
| 4,820,850 A | 4/1989 | Verhoeven et al. |
| 4,916,239 A | 4/1990 | Treiber |
| 5,917,058 A | 6/1999 | Kumar et al. |

*Primary Examiner*—Joseph K. McKane
*Assistant Examiner*—Sonya Wright
(74) *Attorney, Agent, or Firm*—Jacobson Holman PLLC

(57) ABSTRACT

The present invention relates to a process for preparing lovastatin and simvastatin which comprises (1) performing step of a lactonization of mevinic acid and analog thereof compounds in the presence of a dehydrating agent and without an acid catalyst under nitrogen sweep; and then (2) making step of crystals at a high temperature. In the process of the present invention, lovastatin and simvastatin highly purified can be produced in a high yield and especially, heterodimers formed as a by-product can be reduced in an amount remarkably. Therefore, the process of the present invention is convenient and economical.

6 Claims, No Drawings

PROCESS OF LACTONIZATION IN THE PREPARATION OF STATINS

TECHNICAL FIELD

The present invention relates to a process for lactonizing mevinic acid or analog thereof. More particularly, the present invention relates to a process for preparing lovastatin and simvastatin in a high yield which comprises (1) performing a lactonization of mevinic acid and analog thereof compounds in the presence of a dehydrating agent without an acid catalyst under nitrogen sweep; and then (2) making crystals at a high temperature.

BACKGROUND

Hypercholesterolemia is known as to be one of the prime risk factors for ischemic cardiovascular disease, such as arteriosclerosis. Bile acid sequestrants have been used to treat these diseases. They seem to be moderately effective but they must be consumed in large quantities, i.e. several grams at a time and they are not very palatable.

Presently, lovastatin and simvastatin, analog of lovastatin, are commercially available as highly active therapeutic agents for anti-hypercholesterolemia. They suppress HMG-CoA reductase, by which the cholesterol biosynthesis is inhibited. These compounds so-called statins are reported to exist in a dihydroxylic acid form with an open circular structure as depicted in Formula 2 and in a lactone form as depicted in Formula 1.

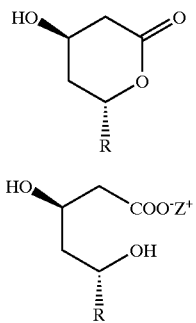

<Formula 1>

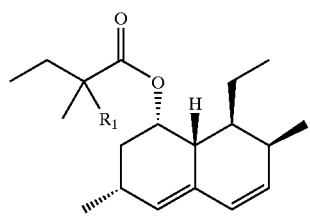

<Formula 2>

Wherein Z is hydrogen, ammonium or metal cation, R is a radical of Formula 3 and $R_1$ is H or $CH_3$.

<Formula 3>

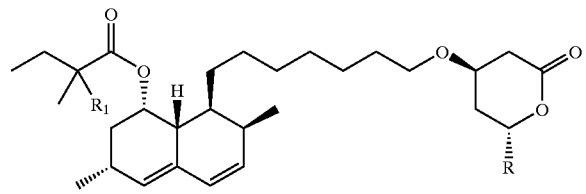

Statins are known to be active in a dihydroxylic acid form physiologically, but usually administered in a lactone form for patients. Therefore, it is necessary to develop an efficient method to perform a lactonization in a high yield. Since the lactonization is an equilibriated process, specific means should be utilized to transfer the equilibrium toward lactones as shown in Reaction Formula 1 in order to produce lactonized products in a high yield.

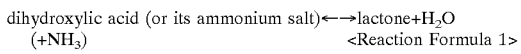

<Reaction Formula 1>

In U.S. Pat. No. 4,820,850, azeotropic distillation or nitrogen sweep were exploited to remove by-products of the reaction (water or ammonia) from reacted mixtures so that the lactonization became almost completed. However, there are several disadvantages in this method.

Precisely, hydroxylic acid substrate works as an acid catalyst and thus reduces a reaction velocity, depending upon the substrate consumed so as to take a longer time period for the reaction and to increase by-products generated. Under such a reaction condition, 3-hydroxylactone, a product is reacted with free acids during the extended period. As a result, heterodimers produced through the esterification between 3-hydroxy group of 3-hydroxylactone and the free acids is increased in the amount as depicted in Formula 1a.

<Formula 1a>

Wherein, R and $R_1$ are defined as described above.

In case that this kind of heterodimers are present, the total yield and the purity of lactone products are decreased. Therefore, the reacted product is diluted in a high degree before use in order to minimize the formation of heterodimers. However, this is also disadvantageous for the efficiency of the reaction.

Furthermore, Korean patent publication No. 97-11286 discloses another process for preparing lactones. It involves treating the free hydroxylic acid or ammonium or metal salt derivatives of mevinic acid or analog thereof in a water miscible organic solvent (especially acetic acid medium) which exhibits a sufficient solubility difference between the hydroxylic acid and lactone, and a strong acid catalyst. After the free hydroxylic acid-lactone equilibrium is established, water is added in an amount sufficient to effect complete crystallization of the lactone from the reaction medium. However, in this method strong acids such as methanesulfonic acid, chloric acid, sulfuric acid, trifluoroacetic acid and the like should be utilized in 1.2~1.5 M and strong bases also should be added in a large amount to neutralize the solution. Therefore, this is not unuseful for industrial application in a large scale as well as very harmful environmentally. Besides, extra water should be supplemented in order to complete the lactonization, but this induces a crystallization again onto the existing crystal, and the obtained crystals of lactone become non-homogeneous. In addition, there are some other problems. Moreover, since the resulting product is not filtrated thoroughly, the procedure for the reaction and the work-up takes a very long time approximately 9~12 hours, which reduces the productive efficiency.

In order to improve the conventional method described above, U.S. Pat. No. 5,917,058 has illustrated the process for the preparing lactones, in which dihydroxy groups of statins or analog thereof, especially in an ammonium salt, are reacted with acetic acid medium without adding an acidic catalyst and without removing water or ammonia at 35~40°

C., and then insoluble solvent such as water, hexane, cyclohexane and the like is added to make lactones. However, in this method acetic acid as a solvent is utilized in 3~7-fold larger amount than that of the reactant and should be neutralized with bases, which the neutral salt (ammonium acetate) is produced and remained in the final lactone compounds. Therefore, another process is required to recrystallize and the process for the preparing lactones becomes inconvenient and uneconomical. The lactone compound and its neutral salts exist in a mixed state and are not filtrated properly, which makes the process inefficient. In addition, extra contaminant, which is formed from the 3-hydroxy group of lactone ring through dehydration, can be observed in an acidic condition under heated state since only acetic acid is used as a solvent. The contaminant will not removed easily by recrystalization and decreases the purity and the yield of lactone compounds.

As demonstrated above, it is necessary to develop new process for preparing lactone compounds in a high purity. Precisely, since lactone compounds are prepared in an equilibriated reaction from mevinic acid or analog thereof, the by-product (water and ammonia) should be removed so as to complete the reaction. As a result, the lactone compound can be obtained in a high yield and through this procedure the produced heterodimers are reduced in the amount.

DISCLOSURE OF INVENTION

The inventors of the present invention have been studied in this field in order to overcome the foregoing and other disadvantages in the conventional methods described above. Consequently, the inventors developed a new process for the lactonization in the preparation of statins so as to solve the existing problems and completed the present invention successfully.

Therefore, the object of the present invention is to provide a process for preparing lactone compounds, which is convenient and economical as well as decreases the content of heterodimers remarkably.

The present invention relates to a process for lactonizing mevinic acid or analog thereof. More particularly, the present invention relates to a process for preparing a compound of Formula 1 which comprises (1) step of performing a lactonization of Formula 2 in the presence of a dehydrating agent and without an acid catalyst under nitrogen sweep; and then (2) step of making lactone product in crystals.

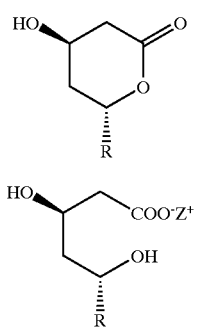

<Formula 1>

<Formula 2>

Wherein, Z is hydrogen, ammonium or metal cation, R is a radical as depicted in Formula 3 and $R_1$ is H or $CH_3$.

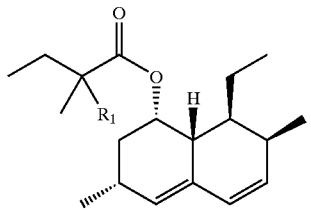

<Formula 3>

Hereinafter, the present invention will be illustrated more clearly.

In the present invention, the dehydrating agent can be one selected among a group comprising magnesium sulfate, sodium sulfate, calcium chloride, molecular sieve and like. Preferably, magnesium sulfate can be used. The dehydrating agent completes the reaction by removing water generated in the equilibriated reaction. As a result, it reduces contaminants of by-products with shortening the period of the reaction time. Therefore, it affects outstandingly to enhance the yield of lactone compounds.

By using the dehydrating agent in the present invention, the time period for the reaction can be reduced to 2~4 hours and preferably to about 3 hours. As a reference, in conventional methods, it takes 5~7 hours. Therefore, the heterodimers (Formula 1a) produced from the esterification between 3-hydroxy group of 3-hydroxylactone as a product and free acids are decreased remarkably when it is compared with the result of the prior arts. Preferably, the amount of the dehydrating agent can be in the range of 1~2 equivalent against 1 M dihydroxy of statin or analog thereof, especially in an ammonium salt form and more preferably in the range of 1.2~1.5 equivalent.

The solvent utilized in the lactonization can be adopted among toluene, ethylacetate, isopropylaceate, acetonitrile, acetone, dichloroethane, chloroform and the like as a neutral organic solvent and preferably selected among toluene, acetonitrile, acetone or dichloroethane. The organic solvent used in the present invention described above consists only one solvent and thus can be used by retrieving the solvent by simply distilling, which contributes to reduce the cost a lot.

The lactonization in the present invention is accomplished under nitrogen sweep at a reflux temperature. The reaction time is adjusted not to exceed 4 hours preferably, since by-products formed increase after more than 4 hours and more preferably, the reaction proceeds for about 3 hours.

The solvent adopted for the crystallization can be one selected among water, ethanol, isopropyl alcohol, n-hexane, cyclohexane, toluene, ethylacetate, isopropylacetate, acetonitrile, acetone, dichloroethane or chloroform or a mixed solvent comprising more than one of these. Preferably, the mixed solvent can be made by blending between ethanol and water or between toluene and cyclohexane.

Preferably, the solvent for the crystallization can be a mixed solvent comprising 8~10 volume portion of water and 8~10 volume portion of ethanol, or a mixed solvent comprising 2~3 volume portion of toluene and 19~21 volume portion of cyclohexane against 1 weight portion of a dihydroxy, especially an ammonium salt of statin and analog thereof. In the present invention, if the solvent amounts of water/ethanol and toluene/cyclohexane are more than this scope, the contaminants might not be removed easily as well as the crystallization of the solid might be lowered, which seems not preferable.

In addition, the process for crystallization is performed preferably at the temperature range of 30~40° C. by using the mixed solvent of water/ethanol and tolene/cyclohexane. As a reference, in case that the temperature for the crystallization is less than 30° C., it is difficult to remove contaminants and in case that it is more than 40° C., it is not preferable since the crystallization of the solid might be lowered. Consequently, the stability is reduced disadvantageously.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of 6(R)-[2-[8(S)-(2,2-dimethylbutylyloxy)-2(S), 6(R)-dimethyl-1,2,6,7,8,8a(R)-hexahydronaphthyl]-1(S)ethyl]-hydroxy-3,4,5,6-tetrahydro-2H-pyrane-2-one (simvastatin)

Ammonium 7-[1,2,6,7,8,8a(R)-hexahydro-2(S), 6(R)-dimethyl-8(S)-(2,2-dimethylbutylyloxy)-1(S)-naphthyl]-3(R), 5(R)-dihydroxyheptanoate (2.42 g, 5.3 mmoles) was refluxed under nitrogen sweep at 100~110° C. for 3 hours with a mixture of toluene (49 ml) and magnesium sulfate (0.48 g, 4.0 mmoles). Then, the reaction mixture was cooled to 25° C. and 2.4 g of activated charcoal was added. Then, the reacted product was stirred for 30 minutes then, filtrated and distilled under a reduced pressure for toluene so as to be adjusted to have 5 ml volume. Afterward, 50 ml of cyclohexane was added to the remained product and heated to 35° C. and stirred for 3 hours. The crystals formed above was filtrated, washed using about 20 ml of toluene/cyclohexane (1:10 (v/v)) and dried under vacuum at 40° C. As a result, 2.12 g (yield: 94.9%) of 6(R)-[2-[8(S)-(2,2-dimethylbutylyloxy)-2(S),6(R)-dimethyl-1,2,6,7,8,8a(R)-hexahydronaphthyl]-1(S) ethyl]-hydroxy-3,4,5,6-tetrahydro-2H-pyrane-2-one (simvastatin) was obtained in 98.5% purity (HPLC). The amount of heterodimers reached 0.17%.

Example 2

Preparation of 6(R)-[2-[8(S)-(2,2-dimethylbutylyloxy)-2(S),6(R)-dimethyl-1,2,6,7,8,8a(R)-hexahydronaphthyl]-1(S)ethyl]-4(R)-hydroxy-3,4,5,6-tetrahydro-2H-pyrane-2-one (simvastatin)

Ammonium 7-[1,2,6,7,8,8a(R)-hexahydro-2(S),6(R)-dimethyl-8(S)-(2,2-dimethylbutylyloxy)-1(S)-naphthyl]-3(R),5(R)-dihydroxyheptanoate (2.42 g, 5.3 mmoles) was refluxed under nitrogen sweep at 100~110° C. for 3 hours with a mixture of toluene (49 ml) and magnesium sulfate (0.48 g, 4.0 mmoles). Then, the reaction mixture was cooled to 25° C. and 2.4 g of activated charcoal was added. Then, the reacted product was stirred for 30 minutes, filtrated and distilled under a reduced pressure. Afterward, 21.2 ml of ethanol was added to the remained product and heated to 40° C. Then, 21.2 ml of water was added dropwisely and stirred for 30 minutes. In case that crystal was made, the resulting solution was cooled to 4° C. and stirred for 2 hours. The crystals formed above was filtrated, washed using about 20 ml of the mixed solvent of water/ethanol (1:1 (v/v)) and then dried under vacuum at 40° C. As a result, 1.97 g (yield: 88.2%) of 6(R)-[2-[8(S)-(2,2-dimethylbutylyloxy)-2(S),6(R)-dimethyl-1,2,6,7,8,8a(R)-hexahydronaphthyl]-1(S)ethyl]-4(R)-hydroxy-3,4,5,6-tetra hydro-2H-pyrane-2-one (simvastatin) was obtained in 98.5% purity (HPLC). The amount of heterodimers reached 0.13%.

Example 3

Preparation of 6(R)-[2-[8(S)-(2-methylbutylyloxy)-2(S),6(R)-dimethyl-1,2,6,7,8,8a(R)-hexahydronaphthyl]-1(S)ethyl]-4(R)-hydroxy-3,4,5,6-tetra hydro-2H-pyrane-2-one (lovastatin).

Excepting using of ammonium 7-[1,2,6,7,8,8a(R)-hexahydro-2(S),6(R)-dimethyl-8(S)-(2-methylbutylyloxy)-1(S)-naphthyl]-3(R),5(R)-dihydroxyheptanoate as a starting material, the same procedure as described in Example 1 were repeated. As a result, 2.05 g (yield: 92%) of 6(R)-[2-[8(S)-(2-methylbutylyloxy)-2(S),6(R)-dimethyl-1,2,6,7,8,8a(R)-hexahydronaphthyl]-1(S)ethyl]-4(R)-hydroxy-3,4,5,6-tetrahydro-2H-pyrane-2-one (lovastatin) was obtained in 98.3% purity (HPLC). The amount of heterodimers reached 0.16%.

Example 4

Preparation of 6(R)-[2-[8(S)-(2-methylbutylyloxy)-2(S),6(R)-dimethyl-1,2,6,7,8,8a(R)-hexahydronaphthyl]-1(S)ethyl]-4(R)-hydroxy-3,4,5,6-tetra hydro-2H-pyrane-2-one (lovastatin)

Excepting using of ammonium 7-[1,2,6,7,8,8a(R)-hexahydro-2(S),6 (R)-dimethyl-8(S)-(2-methylbutylyloxy)-1(S)-naphthyl]-3 (R),5(R)-dihydroxyheptanoate as a starting material, the same procedure as described in Example 2 were repeated. As a result, 1.95 g (yield: 87.5%) of 6(R)-[2-[8(S)-(2-methylbutylyloxy)-2(S),6(R)-dimethyl-1,2,6,7,8,8a(R)-hexahydronaphthyl]-1(S)ethyl]-4(R)-hydroxy-3,4,5,6-tetrahydro-2H-pyrane-2-one (lovastatin) was obtained in 98.6% purity (HPLC). The amount of heterodimers reached 0.13%.

INDUSTRIAL APPLICABILITY

According to the process for preparation of the present invention, lovastatin and simvastatin in a highly purified state can be produced in a high yield and especially, the whole procedure is convenient and economical as well as the amount of heterodimers, by-products can be reduced remarkably.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A method for preparing a compound of Formula 1

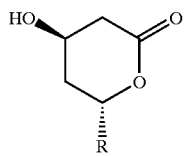

wherein R is a radical of Formula 3

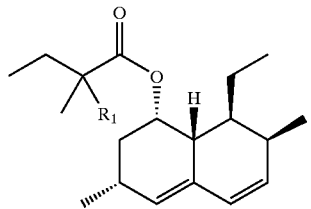

wherein $R_1$ is H or $CH_3$,
which comprises the steps of:
lactonizing a compound of Formula 2

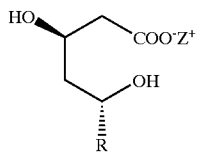

wherein Z is hydrogen, ammonium or metal cation, in the presence of a dehydrating agent under nitrogen sweep and without acid catalyst; and crystallizing the obtained lactone product in a solvent.

2. The method for preparing the compound according to claim 1, in which the dehydrating agent can be more than one selected from a group comprising magnesium sulfate, sodium sulfate, calcium chloride and molecular sieve.

3. The method for preparing the compound according to claim 1, in which the dehydrating agent is utilized in the range of 1~2 equivalent per 1 M compound of Formular 2.

4. The method for preparing the compound according to claim 1, in which a solvent used for crystallization can be one or more than one selected from a group comprising water, ethanol, isopropyl alcohol, n-hexane, cyclohexane, toluene, ethylacetate, isopropylacetate, acetonitrile, acetone, dichloroethane and chloroform.

5. The method for preparing the compound according to claim 4, in which the solvent can be a mixed solvent comprising 8~10 volume portion of water and 8~10 volume portion of ethanol, or a mixed solvent comprising 2~3 volume portion of toluene and 19~21 volume portion of cyclohexane against 1 weight portion of the compound of Formular 2.

6. The method for preparing the compound according to claim 1, in which the process for crystallization is performed at the temperature range of 30~40° C.

* * * * *